(12) United States Patent
Endo et al.

(10) Patent No.: US 6,657,196 B2
(45) Date of Patent: Dec. 2, 2003

(54) METHOD AND APPARATUS FOR ENVIRONMENTAL MONITORING

(75) Inventors: Michiaki Endo, Tokyo (JP); Haruo Yoshida, Tokyo (JP); Yasuhiro Maeda, Tokyo (JP)

(73) Assignee: Advantest Corp., Tokyo (JP)

( * ) Notice: Subject to any disclaimer, the term of this patent is extended or adjusted under 35 U.S.C. 154(b) by 0 days.

(21) Appl. No.: 10/051,527

(22) Filed: Oct. 20, 2001

(65) Prior Publication Data

US 2002/0125433 A1 Sep. 12, 2002

Related U.S. Application Data

(63) Continuation of application No. PCT/JP00/05471, filed on Aug. 16, 2000, now abandoned.

(30) Foreign Application Priority Data

Aug. 19, 1999 (JP) .............................. 11-231495

(51) Int. Cl.[7] .................................................. G01J 5/08
(52) U.S. Cl. ............................. 250/339.11; 250/339.06
(58) Field of Search ....................... 250/339.11, 339.06, 250/339.01, 338.1, 370.06, 503.1; 356/445, 300

(56) References Cited

U.S. PATENT DOCUMENTS

| | | | | |
|---|---|---|---|---|
| 5,321,264 A | * | 6/1994 | Kuwabara et al. ..... | 250/339.11 |
| 5,386,121 A | * | 1/1995 | Barbee et al. ........... | 250/341.8 |
| 5,436,454 A | * | 7/1995 | Bornstein et al. ...... | 250/339.12 |
| 6,166,834 A | * | 12/2000 | Taketomi et al. ............. | 359/13 |
| 6,217,695 B1 | * | 4/2001 | Goldberg et al. ...... | 156/244.17 |
| 6,476,393 B1 | * | 11/2002 | Yoshida et al. .......... | 250/341.8 |
| 2002/0106313 A1 | * | 8/2002 | Tabatabaie-Raissi et al. .... | 422/173 |

FOREIGN PATENT DOCUMENTS

| | | |
|---|---|---|
| JP | 06-502012 | 3/1994 |
| JP | 08-313430 | 11/1996 |
| JP | 11-160317 | 6/1999 |
| JP | 11-176898 | 7/1999 |

* cited by examiner

*Primary Examiner*—David Porta
*Assistant Examiner*—Christine Sung
(74) *Attorney, Agent, or Firm*—Muramatsu & Associates (57) ABSTRACT

An infrared beam is applied into an infrared transmitting substrate 10 disposed in an environment to be measured; the infrared beam which has undergone multiple internal reflections in the infrared transmitting substrate 10 and exited from the infrared transmitting substrate 10 is detected; the detected infrared beam is spectroscopically analyzed to measure a species and/or a quantity of the substance in the environment present near the infrared transmitting substrate 10; and a species and/or a concentration of the substance in the environment to be measured are measured based on the species and/or the quantity of the substance in the environment present near the infrared transmitting substrate 10. Thus, the substances in the environment, such as organic contaminants, etc., present in the atmosphere can be identified, or their concentrations can be measured, with high sensitivity and realtime.

13 Claims, 9 Drawing Sheets

METHOD AND APPARATUS FOR ENVIRONMENTAL MONITORING

This is a continuation of International Application PCT/JP00/05471, with an international filing date of Aug. 16, 2000, now abandoned.

FIELD OF THE INVENTION

The present invention relates to a method and apparatus for environmental monitoring for identifying substances, such as organic contaminants, present in the environmental atmosphere or measuring concentrations of the substances.

BACKGROUND ART

The environmental monitoring, which is made for the purpose of identifying substances present in the environmental atmosphere or measuring concentrations of the substances, is required in various sites.

One example of the environmental monitoring is conducted in clean rooms where semiconductor devices are fabricated.

In fabricating semiconductor devices, various processes are conducted on the surfaces of semiconductor wafers in accordance with the purposes of the processes. In a front end process, a cleaning treatment is made on the surfaces of wafers by a wet cleaning method using various chemicals or deionized water, a dry cleaning method using UV light or plasmas or others, or other methods, and then a surface modifying treatment, such as oxidation, etc., is made. The clean surfaces of wafers exposed in such a cleaning process are generally so reactive with other molecules that silicon atoms on the surfaces bond with hydrogen or oxygen, and oxide films are formed. The surfaces of the semiconductor wafers are thus exposed to environmental atmospheres contacting the semiconductor wafers and transiently change.

Semiconductor processes are performed generally in clean rooms, and many systems are used in many steps. When wafers are unloaded from a system to be transferred from a process to another process, the wafers are exposed to the clean room atmosphere. At this time, the wafers are often not only oxidized by oxygen in the air, but also contaminated with certain kinds of contaminants, e.g., organic substances. The wafers are also contaminated with traces of nitrogen oxides, sulfur oxides, etc. It is said that one contamination source of the organic contamination occurring in the clean rooms is organic substances contained in the air in the clean rooms. It is considered that organic substances contained in building materials of the clean rooms, air filters, wires, pipes, etc. are volatilized to produce the organic substances.

Thus, it is very important that quantities of substances contained in the environmental air in a clean room, where a fabrication process of a semiconductor device are conducted, are monitored to identify emission sources of the substances in the environment or control emission amounts of the substances in the environment, thereby increasing fabrication yields and improving performance of semconductor devices.

The environmental monitoring is required not only in the clean rooms for processes for fabricating semiconductor devices, but also in the air of the real environments where we live. Recently it is known that a group of specific substances called "environmental endocrine disrupter" affects health of humans, and animals and plants. Thus, it is even more necessary to control emission of such substances.

As a conventional method for measuring substances in the atmosphere, e.g., thermal desorption Gas Chromatography/Mass Spectroscopy (GC/MS) is knonw in which substances in the environment are adsorbed by capillary column which is a porous material. The capillary column is heated to release the adsorbed substances, and the released adsorbed substances are identified its species and quantified by mass spectrometric analysis.

However, the above-described conventional measuring method usually takes tens of hours to measure, which makes it difficult to feed back measurement results to the environmental control.

On the other hand, the inventors of the present invention have already proposed an organic contaminant detection method using wafer multiple internal reflection Fourier transform infrared attenuated total reflection spectroscopy (FTIR-ATR) for detecting with high sensitivity organic contaminants staying on the surfaces of wafers (see, e.g., Japanese Patent Application No. Hei 11-95853 (1999). When infrared beam is incident on one end of a wafer at a prescribed incident angle, the infrared beam propagates inside the wafer, repeating total reflections on both surfaces, while the infrared beam penetrates through the wafer surfaces (evanescent wave), and a specific infrared band is absorbed by the organic contaminants staying on the surfaces of the wafer. The propagating light exiting from the other end of the wafer is spectroscopically analyzed by FT-IR to thereby detect and identify the organic contaminants staying on the surfaces of the wafer. In comparison with GC/MS method, this detecting method has the equivalent sensitivity and can perform realtime measurement, as well as simple and economical. Thus, it is considered that application of the multiple internal reflection Fourier transform infrared spectroscopy to the environmental monitoring will make the environmental monitoring highly sensitive and realtime.

SUMMARY OF THE INVENTION

An object of the present invention is to provide a method and apparatus for environmental monitoring which can make realtime measurement of high sensitivity by applying multiple internal reflection Fourier transform infrared attenuated total reflection spectroscopy to the environmental monitoring.

The above-described object is achieved by an environmental monitoring method comprising: applying an infrared beam into an infrared transmitting substrate disposed in an environment to be measured; detecting the infrared beam which has undergone multiple internal reflections in the infrared transmitting substrate and exited; spectroscopically analyzing the detected infrared beam to measure a species and/or a quantity of a substance in the environment present near the infrared transmitting substrate; and measuring a species and/or a concentration of the substance in the environment to be measured, based on the species and/or the quantity of the substance in the environment present near the infrared transmitting substrate.

The above-described object is also achieved by an environmental monitoring method comprising: initializing a surface state of an infrared transmitting substrate disposed in an environment to be measured to remove a substance adhered to a surface of the infrared transmitting substrate, in advance of measurement or upon measurement; applying an infrared beam into the infrared transmitting substrate having the surface state initialized; detecting the infrared beam which has undergone multiple internal reflections in the infrared transmitting substrate and exited; spectroscopically analyzing the detected infrared beam to measure a species and/or a quantity of a substance in the environment present near the infrared transmitting substrate; and measuring a species and/or a concentration of the substance in the environment to be measured, based on the species and/or the quantity of the substance in the environment present near the infrared transmitting substrate.

In the above-described environmental monitoring method it is possible that a UV light is irradiated to the infrared transmitting substrate to remove the substance adhering to the infrared transmitting substrate.

In the above-described environmental monitoring method, it is possible that the infrared beam applied into the infrared transmitting substrate is caused to propagate inside the infrared transmitting substrate in one direction, and the infrared beam exited from an end surface other than an end surface on which the infrared beam was incident is detected.

In the above-described environmental monitoring method, it is possible that the infrared beam applied into the infrared transmitting substrate is caused to propagate inside the infrared transmitting substrate in two directions, and the infrared beam exited from the same end surface on which the infrared beam was incident is detected.

In the above-described environmental monitoring method, it is possible that the infrared transmitting substrate includes at least a first propagation path having a longer propagation distance for the infrared beam, and a second propagation path having a shorter propagation distance for the infrared beam; and the first propagation path is used in measuring the substance in the environment with high sensitivity, and the second propagation path is used in measuring the substance in the environment over a wide spectroscopic wavelength range.

The above-described object is also achieved by an environmental monitoring apparatus comprising: an infrared transmitting substrate to which a substance in an environment to be measured is adhered; an infrared source for applying an infrared beam to the infrared transmitting substrate; an infrared spectrometer for detecting and spectroscopically analyzing the infrared beam which has undergone multiple internal reflections in the infrared transmitting substrate and has exited from the infrared transmitting substrate; and a computer for computing a species and/or a quantity of the substance in the environment present near the infrared transmitting substrate, based on a spectroscopic result given by the infrared spectrometer, and computing a species and/or a concentration of the substance in the environment to be measured, based on the species and/or the quantity of the substance in the environment present near the infrared transmitting substrate.

The above-described object is also achieved by an environmental monitoring apparatus comprising: an infrared transmitting substrate to which a substance in an environment to be measured is adhered; an infrared source for applying an infrared beam to the infrared transmitting substrate; an infrared spectrometer for detecting and spectroscopically analyzing the infrared beam which has undergone multiple internal reflections in the infrared transmitting substrate and has exited from the infrared transmitting substrate; a computer for computing a species and/or a quantity of the substance in the environment present near the infrared transmitting substrate, based on a spectroscopic result given by the infrared spectrometer, and computing a species and/or a concentration of the substance in the environment to be measured, based on the species and/or the quantity of the substance in the environment present near the infrared transmitting substrate; and a substance removing means for removing the substance in the environment adhered to the infrared transmitting substrate to initialize a surface state thereof.

In the above-described environmental monitoring apparatus, it is possible that the substance removing means is a UV light irradiating means for irradiating UV light to the infrared transmitting substrate to thereby remove the substance in the environment adhering to the infrared transmitting substrate.

In the above-described environmental monitoring apparatus, it is possible that the UV light applying means comprises a UV source, and a reflecting mirror having an elliptical cross section which is substantially vertical to a propagation direction of the infrared beam; and the infrared source is positioned near one focus of an elliptical face of the reflecting mirror, and the infrared transmitting substrate is positioned near the other focus.

In the above-described environmental monitoring apparatus, it is possible that the infrared transmitting substrate includes at least a first propagation path having a longer propagation distance for the infrared beam, and a second propagation path having a shorter propagation distance for the infrared beam.

In the above-described environmental monitoring apparatus, it is possible that an incidence optical system for applying the infrared beam to the infrared transmitting substrate, and an exit optical system for causing the infrared beam exiting from the infrared transmitting substrate to the infrared spectrometer are disposed on a side of one end surface of the infrared transmitting substrate.

In the above-described environmental monitoring apparatus, it is possible that the infrared transmitting substrate is formed of a material having a transmission band corresponding to a wave number range of not less than 500 $cm^{-1}$ and not more than 5000 $cm^{-1}$.

According to the present invention, concentrations of substances in the environmental atmosphere can be detected with high sensitivity, and their components can be identified. The measurement by the measuring method according to the present invention is realtime, and measured results can be quickly fed back. Accordingly, sources of organic contamination caused in clean rooms can be identified, and quantities of the contamination can be controlled. The environmental monitoring can be made not only in clean rooms, but also in the air of the actual environments where we live. The present invention is useful in controlling emission of the contaminants.

DETAILED DESCRIPTION OF THE INVENTION

Figure 1A:
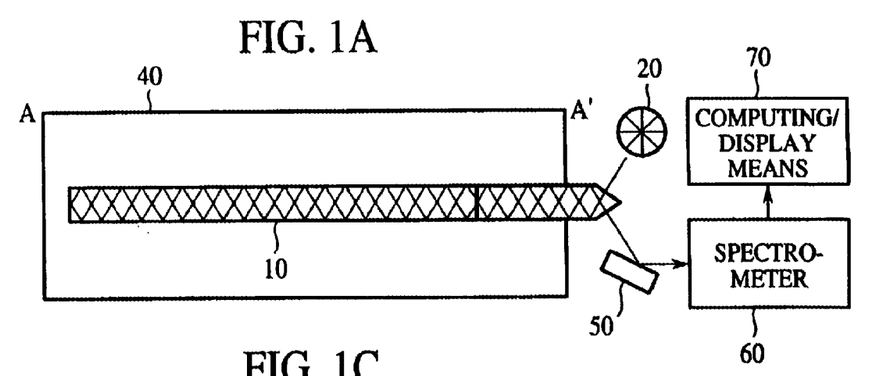
FIGS. 1A–1C are diagrams showing the environmental monitoring method and apparatus according to one embodiment of the present invention, which show a structure thereof.
Figure 1B:
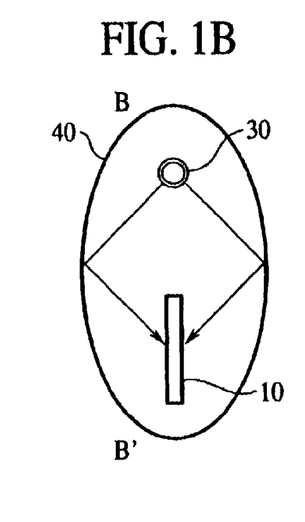
Figure 1C:
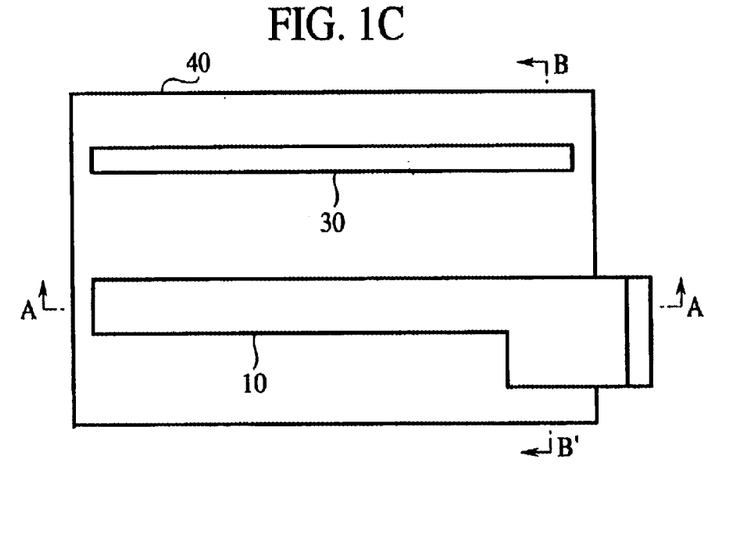
Figure 2:
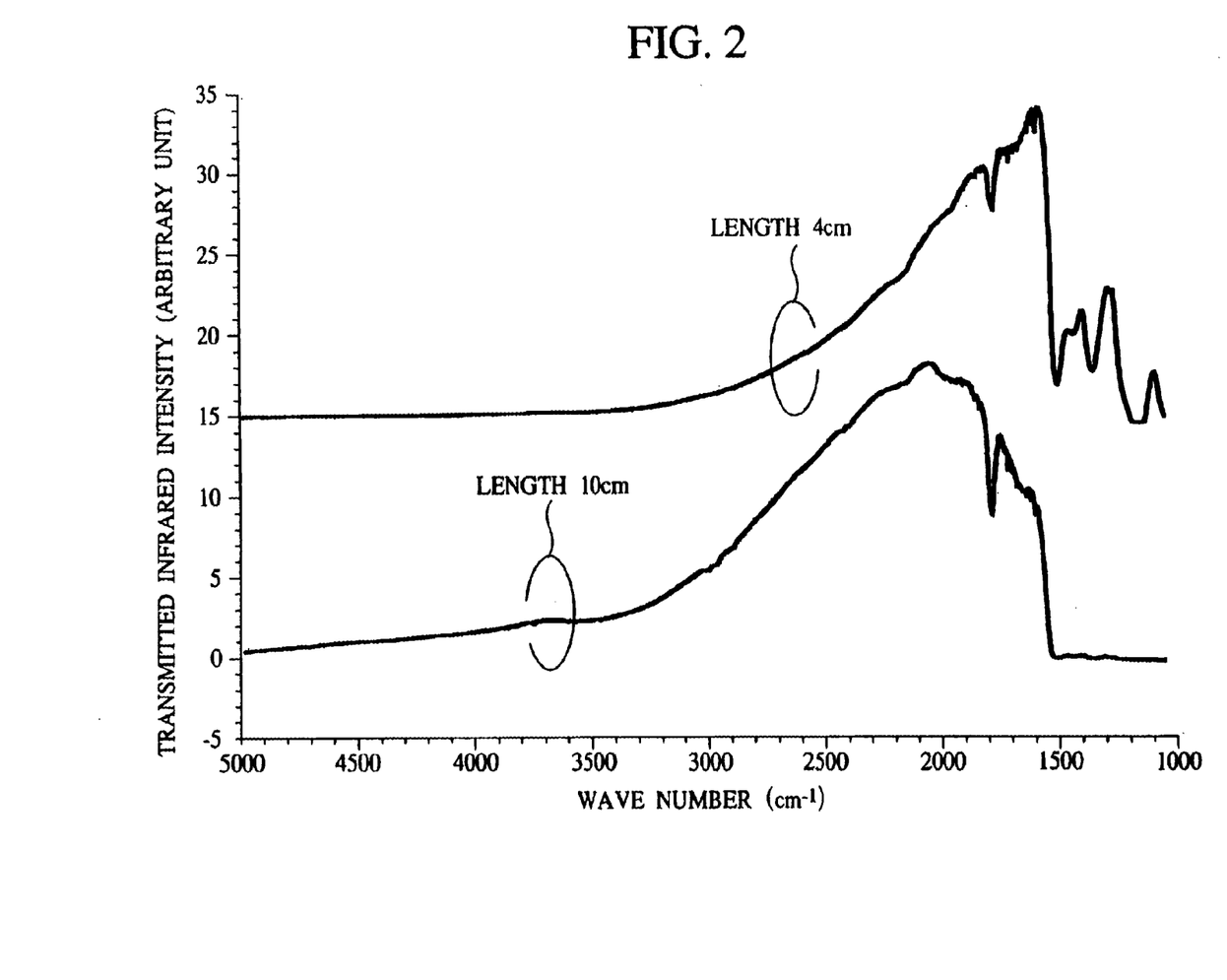
FIG. 2 is a graph of relationships between transmitted intensities of infrared beam which has been transmitted in a 4 cm-length silicon substrate and a 10 cm-length silicon substrate, and wave number.
Figure 3A:
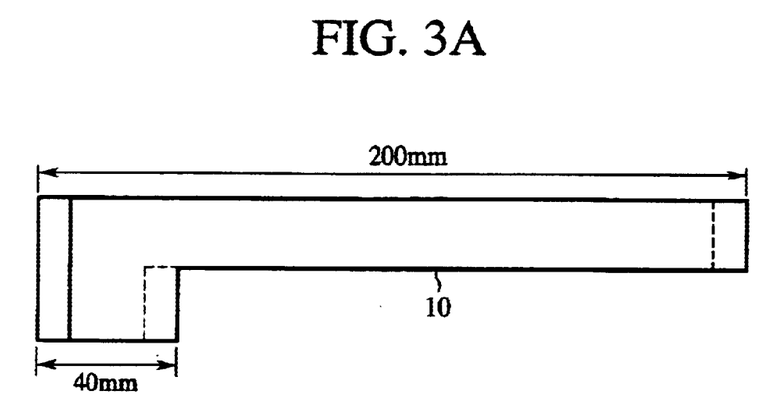
FIGS. 3A–3B are a plan view and a side view of one example of infrared transmitting substrates.
Figure 3B:
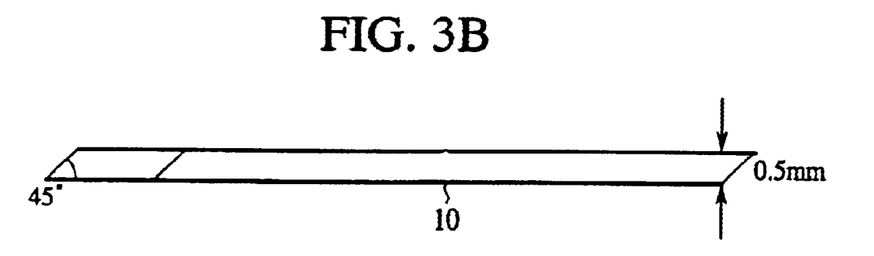
Figure 4:
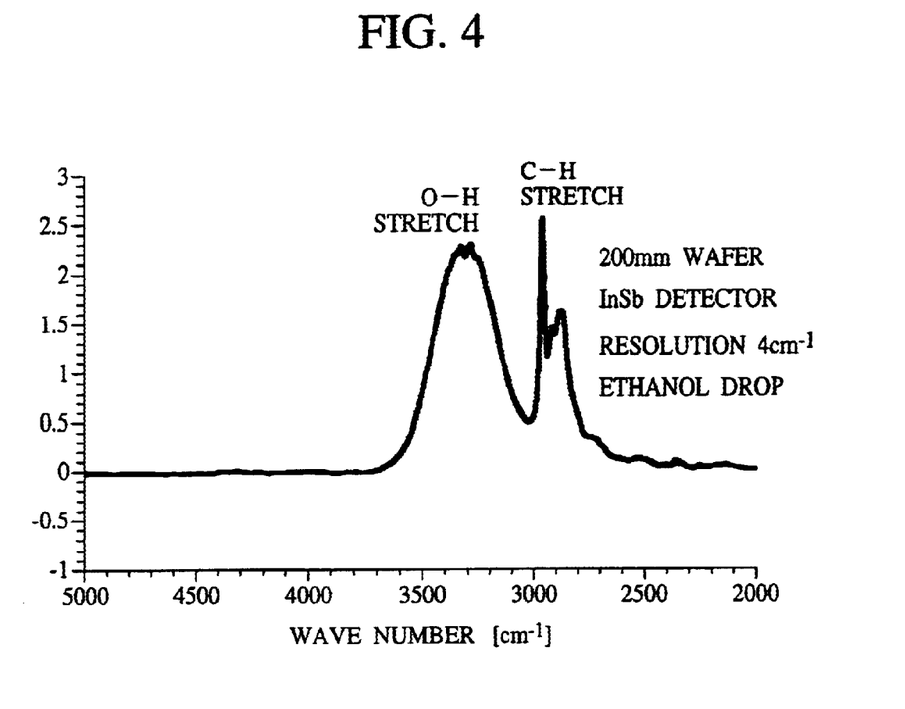
FIG. 4 is a graph of absorbance spectra of ethanol given by multiple internal reflection in a 200 mm-diameter silicon wafer.
Figure 5:
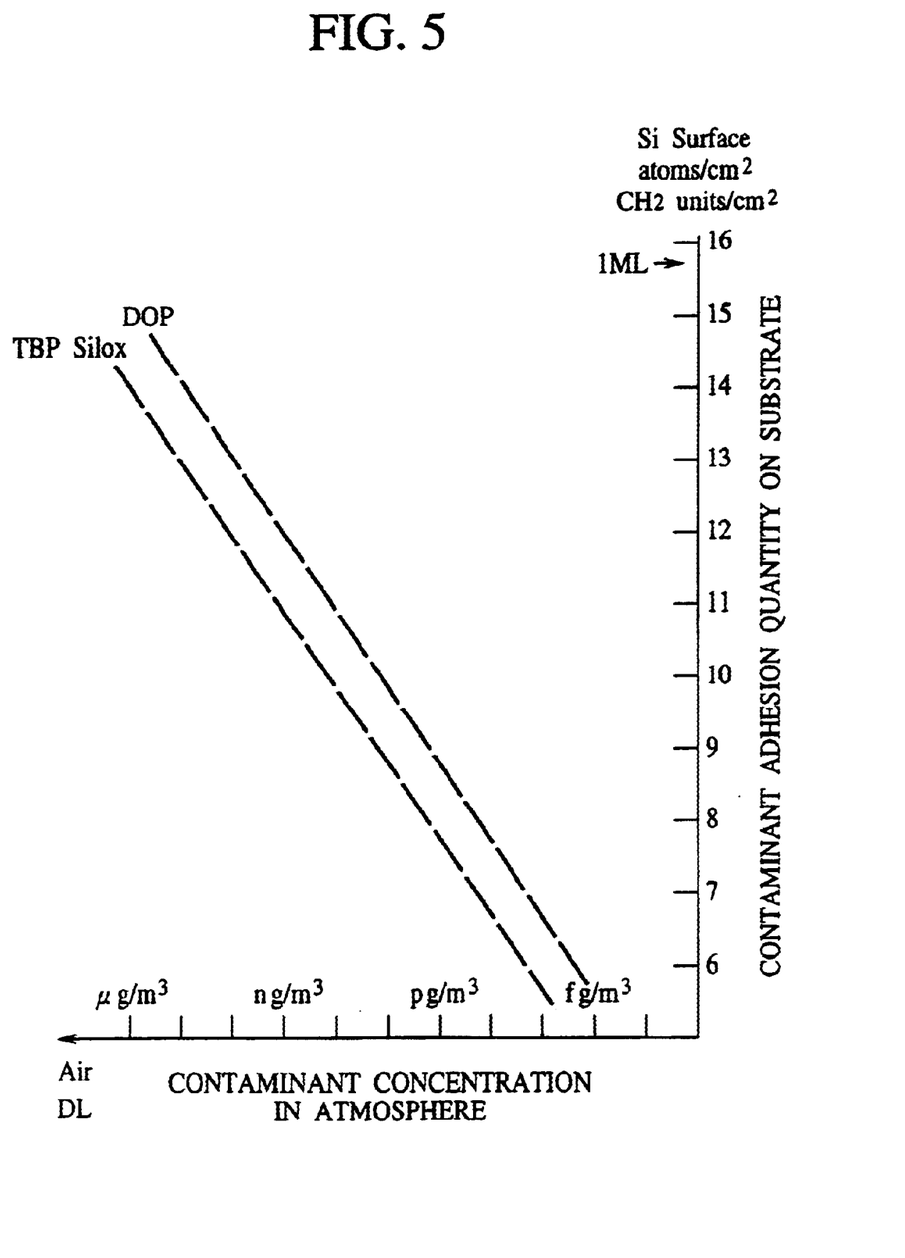
FIG. 5 is a graph of relationships between concentrations of substances in the environmental atmosphere and adhesion amounts of the substances per a unit area of a silicon surface, where the substances have adhered to the silicon surface while the silicon has stood in the atmosphere for 24 hours.
Figure 6:
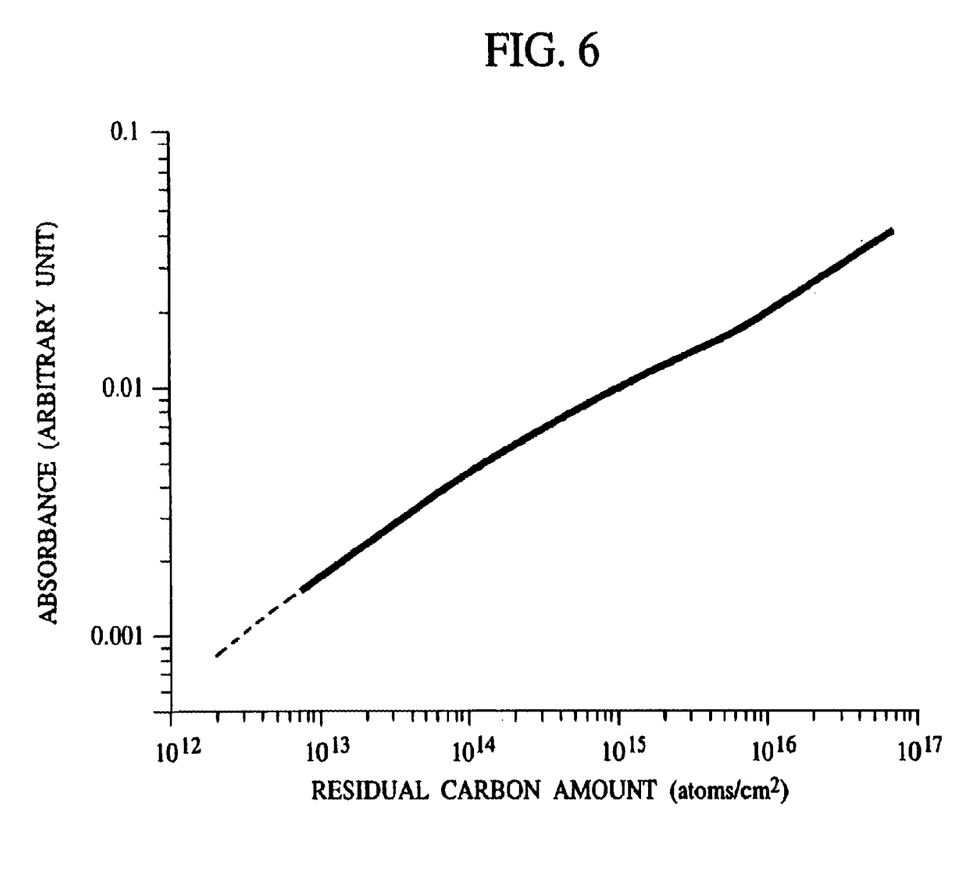
FIG. 6 is a graph of relationships between absorbances and DOP adhesion amounts (converted into carbon amounts).
Figure 7:
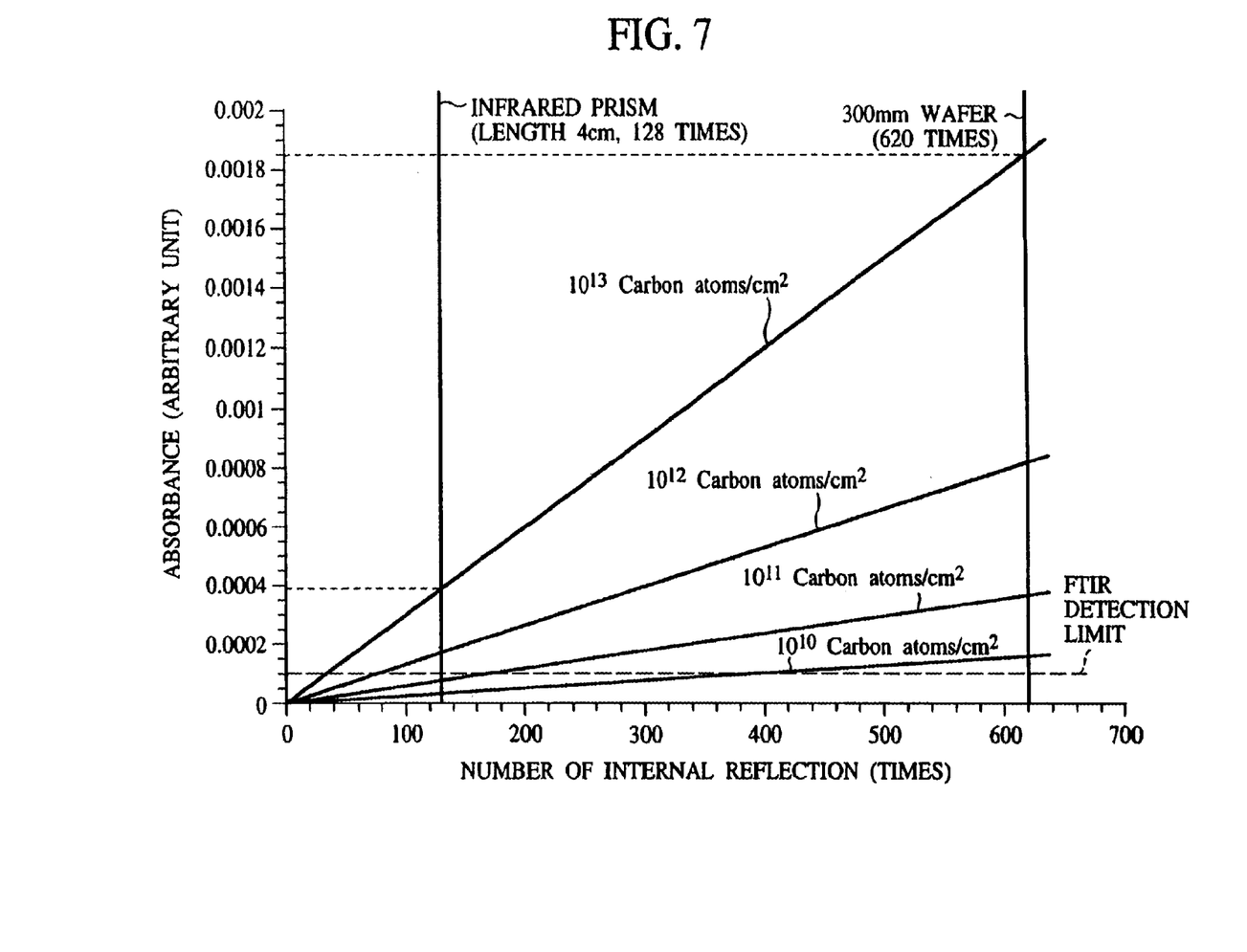
FIG. 7 is a graph of relationships between absorbances and number of multiple internal reflection.
Figure 8:
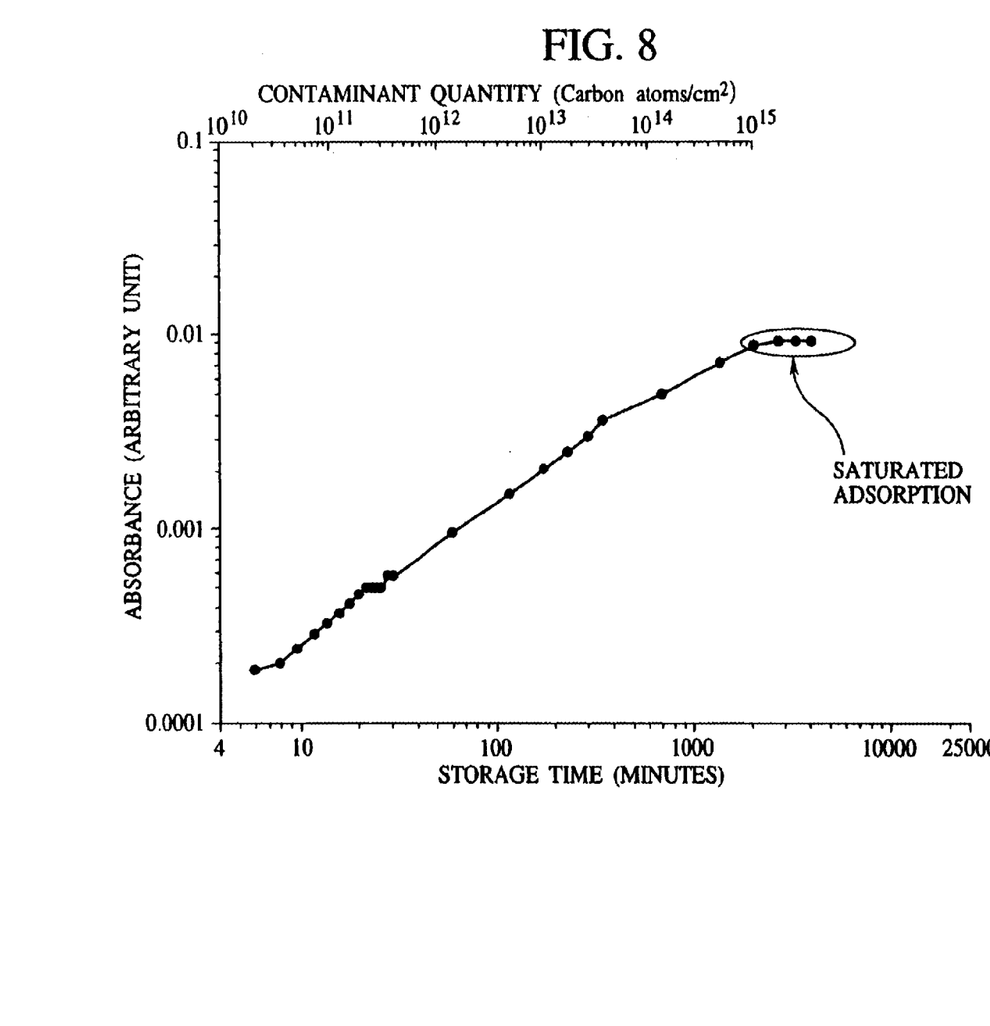
FIG. 8 is a graph of relationships between absorbances, storage time and contamination amounts.

The environmental monitoring method and apparatus according to one embodiment of the present invention will be explained with reference to FIGS. 1 to 8. FIGS. 1A–1C are diagrammatic views of the environmental monitoring method and apparatus according to the present embodiment, which show a structure thereof. FIG. 2 is a graph of relationships between transmitted intensities of infrared beam which has been transmitted in a 4 cm-length silicon substrate and a 10cm-length silicon substrate, and wave number. FIGS. 3A–3B are a plan view and a side view of one example of infrared transmitting substrates. FIG. 4 is a graph of absorbance spectra of ethanol given by multiple internal reflection in a 200 mm-diameter silicon wafer. FIG. 5 is a graph of relationships between concentrations of substances in the environmental atmosphere and adhesion amounts of the substances per a unit area of a silicon surface, in which the substances have adhered to the silicon surface while the silicon has stood in the atmosphere for 24 hours. FIG. 6 is a graph of relationships between absorbances and DOP (dioctyl phthalate) adhesion amounts. FIG. 7 is a graph of relationships between absorbances and the number of multiple internal reflection. FIG. 8 is a graph of relationships between absorbances, storage time and contamination amounts.

[1] General Structure of the Environmental Monitoring Apparatus

The structure of the environmental monitoring apparatus according to the present embodiment will be explained with reference to FIGS. 1A–1C. FIG. 1A is a cross-sectional view of the environmental monitoring apparatus according to the present embodiment, which shows the structure. FIG. 1B is a sectional view along a plane vertical to a propagating direction of an infrared beam. FIG. 1C is a plan view along a plane parallel with the propagating direction of the infrared beam. FIG. 1A corresponds to the sectional view along the line A–A' in FIG. 1C, and FIG. 1B corresponds to the sectional view along the line B–B' in FIG. 1C.

As shown in FIGS. 1A–1C, the environmental monitoring apparatus according to the present embodiment comprises: an infrared transmitting substrate 10 which adsorbs the measurement substances in the environmental atmosphere-to-be-measured, an infrared source 20 which applies an infrared beam into the infrared transmitting substrate 10 to cause multiple internal reflections, a UV source 30 which removes the substances adhered to the surfaces of the infrared transmitting substrate 10 to initialize the surface state, a reflecting mirror 40 efficiently applying UV light emitted by the UV source 30 to both surfaces of the infrared transmitting substrate 10, a detection optical system 50 which detects transmitted infrared beam which has exited the infrared transmitting substrate 10 after the multiple reflections inside the infrared transmitting substrate 10, a spectrometer 60 which form spectra of infrared beam detected by the detection optical system 50, and computing/display means 70 which identifies substances in the environmental atmosphere-to-be-measured and/or computes concentrations of the substances in the environment, based on analysis results of the spectrometer 60.

The constituent members of the environmental monitoring apparatus according to the present embodiment will be detailed below.

(a) Infrared Transmitting Substrate 10 As described above, the infrared transmitting substrate 10 adsorbs substances in the environmental atmosphere-to-be-measured for the measurement. The infrared transmitting substrate 10 must be of a material which transmit light of wavelength ranges corresponding to molecular vibrations of substances-to-be-measured. Wave number ranges corresponding to fundamental vibrations of organic substances, which are typical substances in the environment, are in the infrared/near infrared region of 500 cm$^{-1}$ (wavelength 20 $\mu$m)–5000 cm$^{-1}$ (wavelength 2 $\mu$m). Accordingly, a material of the infrared transmitting substrate 10 is selected out of a group of infrared transparent materials which can transmit light of the wave number range (wavelength range).

Silicon (Si) has a transmitting wavelength range of an about 1.2–6 $\mu$m, and can be selected as a material forming the infrared transmitting substrate 10. A suitable configuration of the infrared transmitting substrate 10 for the environmental monitoring apparatus according to the present embodiment will be explained with an example in which the infrared transmitting substrate 10 is formed of silicon.

In order to measure traces of substances present in the environmental atmosphere realtime and with high sensitivity, the substances in the environment adsorbed on the infrared transmitting substrate 10 must be measured with high sensitivity in a short period of time. In comparison with the multiple internal reflection FT-IR method described in Japanese Patent Application No. Hei 11-95853 (1999) filed by the assignee of the present application, which uses a 300 mm-diameter silicon wafer, hundreds times of internal reflections will be necessary to detect traces of organic substances present in the atmosphere in an about 10 minutes–1 hour monitoring period of time.

Number of internal reflection N is expressed by $$N = L/d \cdot \tan \theta_{int}$$

where L represents a total length of the infrared transmitting substrate 10; d represents a thickness of the infrared transmitting substrate 10; and $\theta_{int}$ represents an angle of the internal reflection. A length L of the infrared transmitting substrate 10 is preferably within severak tens of cm at the longest in consideration of fabricating infrared absorption of the material forming the infrared transmitting substrate 10 and practical dimensions of the environmental monitoring apparatus. For a larger number of internal reflection it is necessary to reduce the thickness of the infrared transmitting substrate 10 to an extent that the intensity of the infrared transmitting substrate 10 is not deteriorated. In order to prevent the infrared beam from scattering upon multiple internal reflections it is necessary that the infrared transmitting substrate 10 has both surfaces polished.

As a substrate material, an 8 inch-diameter silicon wafer which is currently used in semiconductor processes is considered. The 8 inch-diameter silicon wafer has a 0.5 mm-thick and a 200 mm-diameter. When angle of the internal reflection is 45E, internal reflections can be 400 times. These number of internal reflection are substantially equal to the times (387 times) provided by a 300 mm-diameter silicon wafer of a 0.775 mm-thick, and a sensitivity equal to that provided by the multiple internal reflection Fourier transform infrared spectroscopy using a 300 mm-diameter wafer can be provided.

Further, the inventors of the present application have made it experimentally certain that when the infrared beam is transmitted in the silicon substrate, whose infrared beam propagation length is long, infrared transmission spectra on the longer wavelength side are absorbed and cannot be observed.

FIG. 2 shows measurement results of multiple internal reflection spectra of infrared beam transmitted through a 4 cm-length silicon substrate and a 10 cm-length silicon substrate. It is seen that the substrate of a 4 cm-length can provide spectra up to about 1000 cm$^{-1}$, while the substrate of a 10 cm-length can provide no spectrum on the side of the smaller wave numbers (longer wavelength side) than about 1500 cm$^{-1}$. In order to identify substances by infrared absorption, spectra on the side of larger wave numbers than 1000 cm$^{-1}$ will be necessary. Accordingly, to this end, a length of the substrate must be limited to several centimeters.

In order to achieve a high sensitivity and a wide measurement wave number range compatible with each other when the infrared transmitting substrate 10 is formed of a material whose absorption of infrared spectrum takes place on a longer wavelength side, as does in silicon, the infrared transmitting substrate 10 of the configuration as exemplified in FIGS. 3A–3B can be used. The substrate is formed in a stepped structure having a 20 cm-length propagation path and a 4 cm-length propagation path. For the measurement of high sensitivity, the 20 cm-length propagation path can be used to cause the multiple internal reflections. For the identification of species of substances, the 4 cm-length propagation path can be used to cause the multiple internal reflections. Preferably, the end surfaces of the infrared transmitting substrate 10 are polished to be inclined by 45E so as to suppress occurrence of fringes on the multiple internal reflection spectra due to retro-reflection on the end surfaces.

What has been formed based on the basic concept of the infrared transmitting substrate 10 shown in FIGS. 3A–3B, from the viewpoint of a simplified constitution, etc. is the infrared transmitting substrate 10 shown in FIGS. 1A–1C. The infrared transmitting substrate 10 shown in FIGS. 1A–1C has the incident end surface formed in a triangle whose summit angle is 90E and the other end surface formed vertical. In the thus structured substrate, an infrared beam applied to the beam incident end surface of the substrate is reflected on the end surface opposite to the beam incident end surface and returns to the beam incident end surface, and the number of reflections per a unit length can be doubled.

Accordingly, a length of the substrate can be substantially a half of the lengths of those of the basic structure of the infrared transmitting substrate shown in FIGS. 3A–3B, and sensitivity of substantially the same level can be achieved. In this substrate, the incidence of infrared beam, and detection are performed on the same side, and two measurement modes using the longer optical path and the short optical path can be used by applying an infrared beam to incident positions which are slightly offset from each other. This substrate provides an advantage that two modes of incidence and detection can be provided by one and the same optical system. What has been described above makes it possible to miniaturize and simplify the apparatus without lowering the performance.

The infrared transmitting substrate 10 shown in FIGS. 1 and 3 has two propagation distances of infrared beam but may have three or more propagation distances.

In the above description, a material of the infrared transmitting substrate 10 is exemplified by silicon. Substances besides silicon, which can be used as materials of the infrared transmitting substrate 10 are potassium bromide (KBr: transmitting wavelength range 0.4–22 µm), potassium chloride (KCl: transmitting wavelength range 0.3–15 µm), zinc selenide (ZnSe: transmitting wavelength range 0.6–13 µm), barium fluoride (BaF$_2$: transmitting wavelength range 0.2–5 µm), cesium bromide (CsBr: transmitting wavelength range 0.5–30 µm), germanium (Ge: transmitting wavelength range 2–18 µm), lithium fluoride (LiF: transmitting wavelength range 0.2–5 µm), calcium fluoride (CaF$_2$: transmitting wavelength range 0.2–8 µm), sapphire (Al$_2$O$_3$: transmitting wavelength range 0.3–5 µm), cesium iodide (CsI: transmitting wavelength range 0.5–28 µm), magnesium fluoride (MgF$_2$: transmitting wavelength range 0.2–6 µm), thallium bromide (KRS-5: transmitting wavelength range 0.6–28 µm), zinc sulfide (ZnS: transmitting wavelength range 0.7–11 µm), etc.

It is preferable that a material forming the infrared transmitting substrate 10 is selected suitably in accordance with a wavelength corresponding to molecular vibrations of substances to be measured. It is also preferable that a configuration of the infrared transmitting substrate 10 is adjusted suitably corresponding to properties of a material forming the infrared transmitting substrate 10.

(b) Infrared Source 20

The infrared source 20 can be a light source which emits an infrared beam of a 2 to 25 µm band corresponding to the molecular vibrations of organic molecules. For example, heat rays emitted by applying current to silicon carbide (SiC) filaments or wire made of an alloy of nickel and chrome as a filament may be used as the infrared source 20. The infrared source using SiC emits the infrared beam of a 1.1–25 µm band and is characterized in that such source does not burn when used naked in the air.

A reflection plate of a suitable configuration may be provided for the purpose of improving the performance of the light source and increase the intensity of the infrared beam. For example, various infrared sources-described in Japanese Patent Application No. Hei 11-95853 (1999) may be used.

In the environmental monitoring apparatus according to the present embodiment, an infrared beam is caused to undergo multiple internal reflections inside the infrared transmitting substrate 10, to use the beam penetrating onto the surfaces of the substrate when the infrared beam is reflected to detect molecular vibrations of substances in the environment, such as organic contaminants and chemical substances, to thereby measure substances in the environment present near the substrate or adhered to the surfaces of the substrate. Accordingly, the infrared source 20 must be positioned so that the infrared beam incident on the infrared transmitting substrate 10 undergoes multiple internal reflections inside the substrate.

Conditions under which the infrared beam undergoes total reflections inside the substrate are given by Snell's law and energy reflectivity computation. In a case, for example, where the infrared transmitting substrate 10 is formed of silicon, the infrared beam undergoes total reflections in a range of angles 0–72E the infrared beam forms with respect to the substrate plane. Paths of the infrared beam which has formed reflection angles in this range are traced back, and intersections of the paths and the end surface of the infrared transmitting substrate 10 may be taken as the incident point of the infrared beam.

About setting an angle of incidence of the infrared beam, Japanese Patent Application No. Hei 11-95853 (1999) filed by the assignee of the present application provides detailed information.

(c) Detection Optical System 50, Spectrometer 60

The infrared beam exiting the infrared transmitting substrate 10 is introduced into the spectrometer 60 via the detection optical system 50. The spectrometer 60 is, e.g., an FT-IR spectrometer, which forms spectra of infrared beam by the method of Fourier transform spectroscopy using a two-beam interferometer (Michelson interferometer).

When the infrared beam applied into the infrared transmitting substrate 10 undergoes multiple internal reflections, beam penetrating onto the surfaces of the infrared transmitting substrate 10 (evanescent wave) has a frequency which agrees with a molecular vibration frequencies of substances in the environment adhering to the surfaces of the substrate or present near the substrate, the specific infrared band is resonance-absorbed. Thus, the incident infrared beam is caused to undergo multiple reflections in the infrared transmitting substrate 10, whereby the infrared beam reflects information of a surface state of the substrate. Infrared absorption spectra of the infrared beam exiting the infrared transmitting substrate 10 are analyzed to thereby identify species and quantities of the substances in the environment.

FIG. 4 is a graph of spectra of infrared beam formed by Fourier transform spectroscopy, which has made multiple internal reflections in an 8 inch-diameter silicon wafer with ethanol dropped, and has been detected. As shown, peaks are observed in the wave number ranges corresponding to the molecular vibrations of specific organic contaminants, and adhesion quantities of the contaminants can be computed based on the peak intensities.

It is also possible that the spectrometer is disposed before the infrared detector which is sensitive to a wide wavelength range, so that substances in the environment are detected based on absorption of a plurality of wavelength ranges. It is also possible that the infrared detector is sensitive to only a specific wavelength range of a specific substance in the environment, so that only the specific substance in the environment is detected.

The spectrometer may be an infrared spectrometer using a diffraction grating, in place of FT-IR apparatus.

(d) Computing/display Means 70

Measured data of spectra given by the spectrometer 60 are supplied to the computing/display means 70 to be used to identify substances in the environment and compute their quantities.

Species and calibration curves of substances in the environment are stored as a database in a memory of the computing/display means 70. With reference to the data, measured data are quantified. The computing/display means 70 stores as a database relationships between quantities of substances in the environment adsorbed on the surfaces of the infrared transmitting substrate 10 or present near the infrared transmitting substrate 10 and quantities of substances in the environmental atmosphere, so that concentrations of substances in the environmental atmosphere can be computed based on the quantities of detected substances in the environment near the infrared transmitting substrate 10.

The thus-analyzed result can be displayed on the display means as required.

(e) UV Source 30, Reflecting Mirror 40

The environmental monitoring apparatus according to the present invention identifies and quantifies substances in the environment adsorbed on the surfaces of the infrared transmitting substrate 10 to thereby measure the substances in an atmosphere. Quantities of substances in the environment adsorbed on the infrared transmitting substrate 10 are transiently saturated. Accordingly, when changes of concentration of the substance in the environmental atmosphere must be monitored over a long period of time, the cleaning step of periodically removing the substance in the environment adhered to the surfaces of the infrared transmitting substrate 10 is necessary.

The environmental monitoring apparatus according to the present embodiment includes the UV source 30 as cleaning means for removing the substances from the infrared transmitting substrate. The UV source 30 is for decomposing and evaporating substances in the environment, such as organic contaminants, and emits light of energy higher than bonding energies of substances in the environment adhering to the surfaces of the infrared transmitting substrate 10. For example, UV sources, such as Xe (xenon) excimer lights, a low pressure mercury lamp of a 185 nm- and a 254 nm-emission wavelengths, a dielectric barrier discharge excimer lamp of a 172 nm-emission wavelength, etc., can be used. Light having such energies is applied to dissociate bonds of organic contaminants, such as C—C, C—H, C—O, etc., to thereby remove or evaporate the organic contaminants from the surfaces of the infrared transmitting substrate 10.

The reflecting mirror 40 is for efficiently applying the UV light emitted by the UV source 30 to both sides of the infrared transmitting substrate 10. In the environmental monitoring apparatus according to the present embodiment, the reflecting mirror 40 has an elliptical section, as shown in FIG. 1B, which is vertical to the direction of extension of the infrared transmitting substrate 10 and the UV source 30. The reflecting mirror 40 has the elliptical section, and the UV source 30 is disposed near one focus of the ellipse, the infrared transmitting substrate 10 is disposed near the other focus, whereby the UV light emitted by the UV source 30 can be efficiently irradiated to the infrared transmitting substrate 10. The structure is simple.

To remove substances in the environment, chemical or physical removing means, such as chemical liquid treatment or heating treatment of the substrate, or others, may be used other than the above. In the environmental monitoring apparatus according to the present embodiment, reflection and absorption take place on both the upper side and the lower side of the infrared transmitting substrate 10. Thus, both sides of the substrate must be cleaned.

[2] Quantification of Concentration of Substance in Environmental Atmosphere

In the environmental monitoring method according to the present invention, quantities of substances in the environment adhering to the infrared transmitting substrate and present near the substrate are measured by multiple internal reflection infrared spectroscopy and are converted to concentration of the substance in the environmental atmosphere. That is, concentration of the substance in the environmental atmosphere are not directly measured. Accordingly, in order to obtain concentration of substance in the environmental atmosphere it is necessary to establish in advance relationships between concentrations of the substances in the environmental atmosphere and absorbances of absorption peaks to prepare calibration curves. It is not essentially necessary to compute absolute values of quantities of adhesion to the substrate.

For obtaining calibration curves indicating relationships between concentrations of the substances in the environmental atmosphere and intensities of absorbances, their relationships will be discussed.

As concentration of substance in the environmental atmosphere is higher, more substances adhere to the substrate. When concentration of the substance in the environmental atmosphere increases, the substances in the environment adhere to the substrate in larger quantities. The following relational expression holds between concentrations of the substances in the environmental atmosphere and quantities of the substances in the environment adhering to the substrate when an concentration substance in the environmental atmosphere is represented by C, a conversion coefficient between the adhesion quantity and the concentration is represented by $K_1$, and an adhesion quantity of the substance in the environment to the substrate is represented by W:

$$C = K_1 \times W \quad (1)$$

A transmitted beam intensity I after the substrate has been contaminated can be expressed by the following formula when a transmitted beam intensity before the substrate is contaminated is represented by $I_0$, number of internal reflection are represented by N, and an absorption coefficient per a unit adhesion quantity for a single reflection is represented by $\alpha$:

$$I = I_0 \times \exp(-W \times N \times \alpha). \quad (2)$$

An absorbance A is expressed by $$A = -\log_{10}(I/I_0). \quad (3)$$

An absorbance A can be rewritten by using Equation (2) and Equation (3):

$$A \alpha W \times N \times \alpha \quad (4)$$

Accordingly, Equation (1) can be rewritten to be the following equation when a conversion coefficient between an absorbance and a concentration is represented by $K_2$:

$$C = K_2 \times A \quad (5)$$

Equation (1) and Equation (5) show that an adhesion quantity of a substance in the environment adhered to the substrate, a concentration of the substance in the environment and an absorbance have the proportional relationship with one another. Accordingly, a quantity of a substance in the environment adhered to the substrate exposed to the atmosphere is given based on the absorbance, and the quantity is multiplied by a conversion coefficient to thereby compute a concentration of the substance in the environmental atmosphere.

A conversion coefficient can be measured by, e.g., the following procedures:

1) Expose the substrate in a space where substances are present in predetermined concentrations;
2) measure concentrations of the substances in the environmental atmosphere by another method (a gas detection tube, gas chromatography or others);
3) measure absorbances of absorption peak by the substance in the environment adhering to the substrate by multiple internal reflection method; and
4) repeat the above-described procedures 1) to 3) for spaces having a plurality of concentrations of the substances in the environment, and obtain a conversion coefficient, based on ratios between results of the procedure 2) and those of the procedure 3).

It is preferable that a period of substrate exposing time is the same. When periods of substrate exposing time are different, different adhesion quantities are often resulted for the same concentration of the substance in the environment, and in such case, an intensity of absorbance must be converted so that the periods of substrate exposing time are made equal. To this end, it is necessary that with the substrate exposed in the atmosphere, absorbances are measured at a suitable interval to obtain relationships between periods of substrate exposing time and intensities of absorbance.

To make the measurement correct, it is necessary that conditions for the internal reflection are equal. An infrared beam must be incident on one and the same substrate or substrates of the same configuration under the same conditions. The absorption coefficient is different depending on species of substances in the environment, and for the correct quantification, conversion coefficients must be established in advance for all substances to be measured.

When an adhesion quantity per a unit area on the substrate is computed, a calibration curve is prepared in advance by the following procedures:

1) Prepare a plurality of solutions of substances of different concentrations diluted with a volatile solvent;
2) apply predetermined amounts of the solutions to the substrates;
3) let the substrate with the solutions applied to stand for a suitable period of time to evaporate the solutions;
4) measure by the multiple internal reflection method absorbance of absorption peaks by contaminants adhered to the substrate;
5) compute adhesion quantities of the substances per a unit area, based on the concentration of the solutions, the application amounts and areas of the substrate; and
6) prepare a calibration curve, based on relationships between the adhesion quantities and absorbances.

Absorbances given by exposing the substrate in the atmosphere are compared with the calibration curve to thereby obtain absolute quantities of the substances in the environment adhered to the substrates.

FIG. 5 is a graph of relationships between concentrations of chemical contaminants in the atmosphere after 24 hours of exposure and contamination of the surfaces of silicon wafer. FIG. 5 shows that, in DOP (dioctyl phthalate), when a wafer was left for 24 hours in an atmosphere of, DOP of a 1 $ng/m^3$ concentration, an adhesion quantity of the DOP to the surfaces of the wafer was $10^{12}$ $CH_2$ $unit/cm^2$. Reversely, it is shown that when an adhesion quantity to the wafer surfaces after 24 hours of exposure was $10^{12}$ $CH_2$ $unit/cm^2$, a DOP concentration in the atmosphere was 1 $ng/m^3$. As shown in TBP (tributyl phosphate: flame retardant), siloxane (volatile matter from silicon calking agent), relationships between concentrations in the atmosphere and adhesion quantities differ depending on conditions, such as species of contaminants, periods of exposure time, etc. Accordingly, it is necessary to establish in advance relationships between concentrations in the atmosphere and adhesion quantities for respective substances to be measured.

Calibration curves as shown in FIG. 5 are prepared in advance and stored in the computing/display means 70, so that concentrations of substances present in the environmental atmosphere can be computed based on adhesion quantities of substances in the environment adhered to the infrared transmitting substrate 10. In place of the calibration curves shown in FIG. 5, calibration curves indicating relationships between concentrations of the substances in the environmental atmosphere and absorbances of absorption peaks are prepared in advance and stored in the computing/display means 70 so as to compute concentrations of substances present in the environmental atmosphere.

[3] Detection Sensitivity

FIG. 6 shows intensity changes of absorbance of C—H absorption corresponding to adhesion quantity changes of DOP measured by 300 mm-diameter wafers. The measuring conditions were a 32° internal reflection angle and 620 internal reflection times. DOP is one of plasticizers for plastics, and is one of the substance contained in the atmosphere of clean rooms and known as an environmental endocrine disrupter. As described above, number of multiple internal reflection of the 200 mm-diameter silicon substrate and that of the 300 mm-silicon substrate are substantially equal to each other. For the configuration of the infrared transmitting substrate 10 of the present embodiment, substantially the same relationships will hold. When an intensity of infrared absorption is simply considered to be proportional to number of reflection, a value of the absorbance at 620 reflection times and the origin are linearly interrelated with each other, whereby relationships between number of internal reflection and detection sensitivity can be derived. These relationships are shown in FIG. 7. Concentrations of below $10^{12}$ carbon atoms/cm$^2$ are given by extrapolated calibration curves.

Detection sensitivity of the measuring method according to the present embodiment can be given in comparison with sensitivity of the FT-IR apparatus used in forming spectra of infrared beam. A detection limit of the absorbance of the FT-IR apparatus used by the inventors of the present application is about 0.0001, and an about $10^{10}$ carbon atoms/cm$^2$ adhesion quantity on 200 mm-diameter silicon substrates can be measured. When multiple internal reflections are made on a 4 cm-length position at the same internal reflection angle, number of internal reflection are 128 times, and an about $10^{12}$ carbon atoms/cm$^2$ adhesion quantity can be measured.

A 300 mm-diameter silicon wafer was left in a clean booth enclosed by a polyvinyl chloride curtain, and transient changes of absorbance of organic substances released from polyvinyl chloride, paints of the clean booth, etc., which adhered to the wafer were observed. The results are shown in FIG. 8. Contaminant quantities of the adhering organic substances obtained based on the calibration curves shown in FIG. 6 are taken on the upper axis of FIG. 8. As seen in FIG. 8, it is found that the adhesion of the organic substances by the atmosphere makes substantially no change after 48 hours. This is because the adhesion of the contaminants is saturated, and the adhesion of the contaminants and re-release of the contaminants are in equilibrium (saturated adsorption) and does not mean that the contaminants have been eliminated. Thus, in investigating changes of contaminant concentrations in the atmosphere for a long period of time, the periodic cleaning by UV light as described above is necessary. A saturated adhesion quantity at this time is estimated to be $10^{15}$ carbon atoms/cm$^2$. This quantity is enough to be detected at the 4 cm-length position. Based on this, the substrate of the present invention is left to stand until a saturated adsorption quantity, whereby substances in the environment adhering to the substrate can be identified.

As described above, the substrate configuration of the present invention can provide sensitivity and a measurement wavelength range sufficient to detect substances in the environmental atmosphere.

[4] Environmental Monitoring Method

The environmental monitoring method according to the present embodiment will be explained with reference to FIGS. 1A–1C.

First, the environmental monitoring apparatus according to the present embodiment is disposed in an environment to be monitored.

Then, an infrared beam emitted by the infrared source 20 is applied into the infrared transmitting substrate 10. The infrared beam applied into the infrared transmitting substrate 10 undergoes multiple internal reflections on the back and front surfaces of the infrared transmitting substrate 10 while probing to accumulating information of substances in the environment adsorbed on the surfaces of the infrared transmitting substrate 10, and exits outside.

For higher-sensitivity measurement of substances in the environment, it is preferable that the infrared beam is incident on the longer-distance portion of the infrared transmitting substrate 10 so as to increase times of the multiple internal reflections in the infrared transmitting substrate 10 for higher detection sensitivity. On the other hand, for the detection of substances in the environment over a wide spectroscopic wavelength range, it is preferable that the infrared beam is incident on the shorter-distance portion of the infrared transmitting substrate 10 so as to avoid attenuation of the infrared beam in the infrared transmitting substrate 10.

Next, the infrared beam exiting the infrared transmitting substrate 10 is detected by the detection optical system 50, then spectroscopically analyzed by the spectrometer 60, and the substances in the environment are identified and quantified by the computing/display means 70.

Then, if necessary, a UV light emitted by the UV source 30 is irradiated on the infrared transmitting substrate 10 via the reflecting mirror 40 so as to remove the substances in the environment adsorbed on the surfaces of the infrared transmitting substrate 10 to initialize the substrate surfaces.

Next, the above-described measurement is repeated as required to measure transient changes, etc. of substances in environmental atmospheres.

As described above, according to the present embodiment, Fourier transform infrared spectroscopy using multiple internal reflections of infrared beam in the infrared transmitting substrate 10 is used to identify substances in the environmental atmosphere and measure their concentrations. The measurement of environmental contamination can be made with high sensitivity and realtime.

Figure 9:
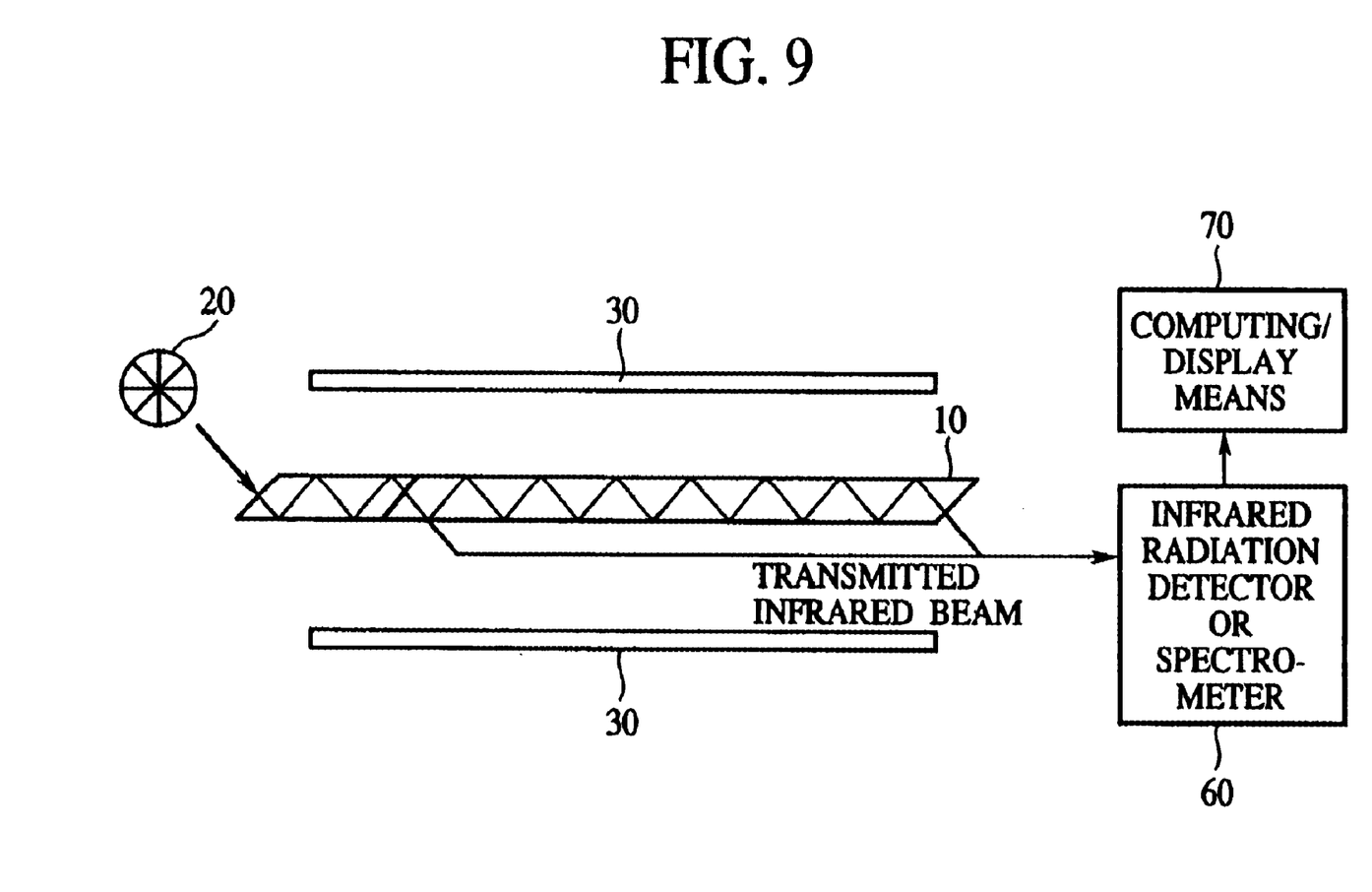
FIG. 9 is a diagrammatic view of the environmental monitoring method and apparatus according to another embodiment of the present invention, which explains the method and the apparatus.

In the above-described embodiment the infrared transmitting substrate 10 shown in FIGS. 1A–1C is used. The infrared transmitting substrate 10 shown in FIGS. 3A–3B may be used, and in this case, as shown in FIG. 9, the infrared beam emitting optical system is disposed on the side of the end surface other than the incidence end surface for the infrared beam to be incident on, and the exiting infrared beam is analyzed.

The reflecting mirror 40 is not essential. As shown in FIG. 9, the UV sources 30 may be disposed on both sides of the infrared transmitting substrate 10.

In the above-described embodiment, DOP as a substance in the environment is detected. The environmental monitoring method and apparatus according to the present invention are applicable to the measurement of other substances in the environment. That is, the environmental monitoring method and apparatus according to the present invention are applicable to the measurement of ester phthalate group, such as DOP (dioctyl phthalate), DBP (dibutyl phthalate), DECP (diethyl chlorophosphate), etc., ester phosphate group, such as TBP (tributyl phosphate), TCEP (tris- (2-carboxyethyl)-phosphate), etc., BHT (butylate hydroxytoluene), low molecular cyclic siloxane group, IPA (isopropyl alcohol), etc., but are not limited to the above. VOC (volatile organic compounds), such as benzene, toluene, ethylbenzene, xylene, trimethylbenzene, chloroform, 2-pinene, acetone, ethanol, ketone group, formaldehyde, etc can be also measured.

The environmental monitoring method and apparatus according to the present invention can detect concentrations of substances in the environmental atmosphere with high sensitivity and identify their components. The measurement is conducted in realtime. The present invention is useful as an environmental monitoring method and apparatus especially for identifying substances in the environment, such as organic contaminants, etc., in the atmosphere or measuring their concentrations.

What is claimed is:

1. An environmental monitoring method comprising:

establishing a relationship between a concentration of a substance in an environment and a quantity of the substance detected on an infrared transmitting substance;

applying an infrared beam into the infrared transmitting substrate disposed in an environment to be measured;

detecting the infrared beam which has undergone multiple internal reflections in the infrared transmitting substrate and exited;

spectroscopically analyzing the detected infrared beam to measure a quantity of the substance in the environment present near the infrared transmitting substrate; and measuring a concentration of the substance in the environment to be measured, based on the quantity of the substance on the infrared transmitting substrate and the relationship with the concentration of the substance established in the foregoing step.

2. An environmental monitoring method comprising:

establishing a relationship between a concentration of a substance in an environment to be measured and a quantity of the substance detected on an infrared transmitting substance;

initializing a surface state of the infrared transmitting substrate disposed in the environment to be measured to remove a substance adhered to a surface of the infrared transmitting substrate, in advance of measurement or upon measurement;

applying an infrared beam into the infrared transmitting substrate having the surface state initialized;

detecting the infrared beam which has undergone multiple internal reflections in the infrared transmitting substrate and exited;

spectroscopically analyzing the detected infrared beam to measure a species and/or a quantity of a substance in the environment present near the infrared transmitting substrate; and measuring a species and/or a concentration of the substance in the environment to be measured, based on the species and/or the quantity of the substance on the infrared transmitting substrate and the relationship with the concentration of the substance established in the foregoing step.

3. An environmental monitoring method according to claim 2, wherein a UV light is applied to the infrared transmitting substrate to remove the substance adhered to the infrared transmitting substrate.

4. An environmental monitoring method according to claim 2, wherein the infrared beam applied into the infrared transmitting substrate is caused to propagate inside the infrared transmitting substrate in one direction, and the infrared beam exited from an end surface other than an end surface on which the infrared beam was incident is detected.

5. An environmental monitoring method according to claim 2, wherein the infrared beam applied into the infrared transmitting substrate is caused to propagate inside the infrared transmitting substrate in two directions, and the infrared beam exited from the same end surface on which the infrared beam was incident is detected.

6. An environmental monitoring method according to claim 2, wherein the infrared transmitting substrate includes at least a first propagation path having a predetermined propagation distance for the infrared beam, and a second propagation path having a propagation distance shorter than that of the first propagation path for the infrared beam; and the first propagation path is used for measuring the substance in the environment with high sensitivity, and the second propagation path is used for measuring the substance in the environment over a wide spectroscopic wavelength range.

7. An environmental monitoring apparatus comprising:

an infrared transmitting substrate to which a substance in an environment to be measured is adhered;

means for establishing a relationship between a concentration of a substance in an environment to be measured and a quantity of the substance detected on the infrared transmitting substance;

an infrared source for applying an infrared beam to the infrared transmitting substrate;

an infrared spectrometer for detecting and spectroscopically analyzing the infrared beam which has undergone multiple internal reflections in the infrared transmitting substrate and has exited from the infrared transmitting substrate; and a computer for computing a quantity of the substance in the environment present near the infrared transmitting substrate, based on a spectroscopic result given by the infrared spectrometer, and computing a concentration of the substance in the environment to be measured, based on the quantity of the substance on the infrared transmitting substrate and the relationship with the concentration of the substance.

8. An environmental monitoring apparatus comprising:

an infrared transmitting substrate to which a substance in an environment to be measured is adhered;

means for establishing a relationship between a concentration of a substance in an environment to be measured and a quantity of the substance detected on the infrared transmitting substance:

an infrared source for applying an infrared beam to the infrared transmitting substrate;

an infrared spectrometer for detecting and spectroscopically analyzing the infrared beam which has undergone multiple internal reflections in the infrared transmitting substrate and has exited from the infrared transmitting substrate;

a computer for computing a species and/or a quantity of the substance in the environment present near the infrared transmitting substrate, based on a spectroscopic result given by the infrared spectrometer, and computing a species and/or a concentration of the substance in the environment to be measured, based on the species and/or the quantity of the substance on the infrared transmitting substrate and the relationship with the concentration of the substance; and a substance removing means for removing the substance in the environment adhered to the infrared transmitting substrate to initialize a surface state thereof.

9. An environmental monitoring apparatus according to claim 8, wherein the substance removing means is a UV light irradiating means for irradiating the UV light to the infrared transmitting substrate to thereby remove the substance in the environment adhered to the infrared transmitting substrate.

10. An environmental monitoring apparatus according to claim 9, wherein the UV light irradiating means comprises a UV source, and a reflecting mirror having an elliptical cross section which is substantially vertical to a propagation direction of the infrared beam; and the UV source is positioned near one focus of an elliptical face of the reflecting mirror, and the infrared transmitting substrate is positioned near the other focus.

11. An environmental monitoring apparatus according to claim 8, wherein the infrared transmitting substrate includes at least a first propagation path having a predetermined propagation distance for the infrared beam, and a second propagation path having a propagation distance shorter than that of the first propagation path for the infrared beam.

12. An environmental monitoring apparatus according to claim 8, wherein an incidence optical system for applying the infrared beam to the infrared transmitting substrate, and an exit optical system for causing the infrared beam exiting from the infrared transmitting substrate to the infrared spectrometer are disposed on a side of one end surface of the infrared transmitting substrate.

13. An environmental monitoring apparatus according to claim 8, wherein the infrared transmitting substrate is formed of a material having a transmission band corresponding to a wave number range of not less than 500 $cm^{-1}$ and not more than 5000 $cm^{-1}$.

* * * * *